US009408705B2

(12) United States Patent
Oosthuizen

(10) Patent No.: US 9,408,705 B2
(45) Date of Patent: Aug. 9, 2016

(54) TIBIAL COMPONENT

(71) Applicant: Christiaan Rudolf Oosthuizen, Johannesburg (ZA)

(72) Inventor: Christiaan Rudolf Oosthuizen, Johannesburg (ZA)

(*) Notice: Subject to any disclaimer, the term of this patent is extended or adjusted under 35 U.S.C. 154(b) by 0 days.

(21) Appl. No.: 14/347,882

(22) PCT Filed: Sep. 28, 2012

(86) PCT No.: PCT/IB2012/055192
§ 371 (c)(1),
(2) Date: Mar. 27, 2014

(87) PCT Pub. No.: WO2013/046170
PCT Pub. Date: Apr. 4, 2013

(65) Prior Publication Data
US 2014/0236308 A1    Aug. 21, 2014

(30) Foreign Application Priority Data

Sep. 29, 2011  (ZA) .................................. 2011/07123

(51) Int. Cl.
*A61F 2/38* (2006.01)
*A61F 2/30* (2006.01)

(52) U.S. Cl.
CPC . *A61F 2/389* (2013.01); *A61F 2/38* (2013.01); *A61F 2/3868* (2013.01); *A61F 2002/30607* (2013.01); *A61F 2002/30884* (2013.01); *A61F 2002/3895* (2013.01)

(58) Field of Classification Search
CPC ......... A61F 2/38; A61F 2/289; A61F 2/2868; A61F 2002/30607; A61F 2002/30884; A61F 2/3872; A61F 2/389; A61F 2002/3895

USPC ............................................ 623/20.27–20.34
See application file for complete search history.

(56) References Cited

U.S. PATENT DOCUMENTS

| 3,774,244 | A | * | 11/1973 | Walker ...................... A61F 2/38 623/20.3 |
| 4,158,684 | A | * | 6/1979 | Klawitter ............ A61F 2/30767 264/261 |
| 4,728,332 | A | * | 3/1988 | Albrektsson .......... A61F 2/3868 623/20.29 |
| 4,795,468 | A | | 1/1989 | Hodorek et al. |

(Continued)

FOREIGN PATENT DOCUMENTS

| EP | 0032828 A2 | 7/1981 |
| FR | 2908039 A1 | 5/2008 |
| GB | 2245175 A | 1/1992 |

OTHER PUBLICATIONS

International Preliminary Report on Patentability for International Application No. PCT/IB2012/055192 dated Jan. 17, 2014.

(Continued)

*Primary Examiner* — Alvin Stewart
(74) *Attorney, Agent, or Firm* — McDonnell Boehnen Hulbert & Berghoff LLP

(57) ABSTRACT

According to one aspect of the present invention, there is provided a tibial component (10), suitable for use in an orthopedic prosthesis, which prosthesis includes a femoral component and a spacer bearing (70), the tibial component comprising a planar tibial plate (15) having an upper bearing surface (30) and a lower attachment surface (20), and the tibial plate further having at least one spacer bearing attachment means for removably securing the spacer bearing to the tibial plate.

19 Claims, 6 Drawing Sheets

(56) References Cited

U.S. PATENT DOCUMENTS

| | | | | |
|---|---|---|---|---|
| 5,766,256 | A * | 6/1998 | Oudard | A61F 2/389 623/20.32 |
| 5,871,541 | A * | 2/1999 | Gerber | A61F 2/3877 623/20.29 |
| 5,871,542 | A * | 2/1999 | Goodfellow | A61F 2/3868 623/20.16 |
| 6,500,208 | B1 * | 12/2002 | Metzger et al. | 623/20.28 |
| 6,506,215 | B1 * | 1/2003 | Letot et al. | 623/20.29 |
| 6,510,334 | B1 * | 1/2003 | Schuster | A61F 2/30942 128/920 |
| 8,105,386 | B2 * | 1/2012 | Perrone et al. | 623/20.29 |
| 8,894,715 | B2 * | 11/2014 | Metzger et al. | 623/20.31 |
| 2002/0082703 | A1 * | 6/2002 | Repicci | A61F 2/3836 623/20.29 |
| 2003/0014122 | A1 * | 1/2003 | Whiteside | 623/20.32 |
| 2003/0100953 | A1 * | 5/2003 | Rosa | A61F 2/38 623/20.3 |
| 2004/0006394 | A1 * | 1/2004 | Lipman | A61F 2/3868 623/20.29 |
| 2004/0064073 | A1 * | 4/2004 | Heldreth | 600/595 |
| 2004/0102852 | A1 * | 5/2004 | Johnson | A61F 2/38 623/20.15 |
| 2004/0167630 | A1 * | 8/2004 | Rolston | A61F 2/38 623/20.14 |
| 2004/0193280 | A1 * | 9/2004 | Webster | A61F 2/3868 623/20.33 |
| 2004/0199249 | A1 * | 10/2004 | Fell | A61F 2/38 623/14.12 |
| 2005/0055100 | A1 * | 3/2005 | Lewis et al. | 623/20.28 |
| 2005/0209703 | A1 * | 9/2005 | Fell | 623/20.33 |
| 2006/0004460 | A1 * | 1/2006 | Engh | A61F 2/30724 623/20.21 |
| 2006/0052875 | A1 * | 3/2006 | Bernero et al. | 623/20.33 |
| 2006/0058883 | A1 * | 3/2006 | Aram | A61B 17/14 623/20.15 |
| 2006/0085078 | A1 * | 4/2006 | Steffensmeier | A61F 2/3868 623/20.29 |
| 2006/0190086 | A1 * | 8/2006 | Clemow | A61F 2/38 623/20.15 |
| 2006/0235517 | A1 * | 10/2006 | Hodorek | A61F 2/30756 623/14.12 |
| 2006/0235537 | A1 * | 10/2006 | Kuczynski | A61F 2/38 623/20.3 |
| 2007/0005142 | A1 * | 1/2007 | Rhodes | A61F 2/389 623/20.32 |
| 2007/0043444 | A1 * | 2/2007 | Lester | 623/20.15 |
| 2007/0129808 | A1 * | 6/2007 | Justin et al. | 623/20.15 |
| 2008/0058945 | A1 * | 3/2008 | Hajaj | A61F 2/38 623/20.14 |
| 2008/0058949 | A1 * | 3/2008 | Dees | A61B 17/155 623/20.35 |
| 2008/0133020 | A1 * | 6/2008 | Blackwell | A61F 2/30721 623/20.34 |
| 2008/0183291 | A1 * | 7/2008 | Scheller | A61F 2/3872 623/14.12 |
| 2008/0243262 | A1 * | 10/2008 | Lee | A61F 2/3868 623/20.33 |
| 2008/0243263 | A1 * | 10/2008 | Lee | A61F 2/3868 623/20.33 |
| 2009/0036984 | A1 * | 2/2009 | Hagen | A61F 2/38 623/14.12 |
| 2010/0016981 | A1 * | 1/2010 | Roger | A61F 2/30721 623/20.32 |
| 2010/0131071 | A1 * | 5/2010 | O'Connor et al. | 623/20.32 |
| 2010/0204801 | A1 * | 8/2010 | Walker | A61F 2/3859 623/20.32 |
| 2010/0274534 | A1 * | 10/2010 | Steines | A61B 17/1675 703/1 |
| 2011/0004316 | A1 * | 1/2011 | Murray | A61B 17/1764 623/20.3 |
| 2011/0015740 | A1 * | 1/2011 | Metzger | A61F 2/38 623/16.11 |
| 2011/0022179 | A1 * | 1/2011 | Andriacchi | A61F 2/38 623/20.18 |
| 2011/0106268 | A1 * | 5/2011 | Deffenbaugh et al. | 623/20.32 |
| 2011/0178607 | A1 * | 7/2011 | Oosthuizen | A61F 2/38 623/20.35 |
| 2011/0319755 | A1 * | 12/2011 | Stein | A61B 5/0031 600/437 |
| 2012/0116524 | A1 * | 5/2012 | Walker | A61B 17/155 623/20.35 |
| 2012/0323333 | A1 * | 12/2012 | Metzger | 623/20.32 |
| 2012/0330429 | A1 * | 12/2012 | Axelson, Jr. | A61F 2/30771 623/20.19 |
| 2013/0053978 | A1 * | 2/2013 | Linares | A61F 2/38 623/23.39 |
| 2013/0079884 | A1 * | 3/2013 | Stein | A61B 5/686 623/18.11 |
| 2013/0166037 | A1 * | 6/2013 | Goodfellow | A61F 2/389 623/20.32 |
| 2013/0317619 | A1 * | 11/2013 | Goodfellow et al. | 623/20.3 |
| 2014/0277548 | A1 * | 9/2014 | Cohen | A61F 2/389 623/20.34 |
| 2014/0330389 | A1 * | 11/2014 | Jordan et al. | 623/20.34 |
| 2015/0305874 | A1 * | 10/2015 | Lloyd | A61F 2/3859 623/20.28 |
| 2015/0342741 | A1 * | 12/2015 | Davignon | A61F 2/389 623/20.32 |

OTHER PUBLICATIONS

Warren, et al., "The supporting structures and layers on the medial side of the knee: an anatomical analysis", J Bone Joint Surg Am, 61:56-62 (1979).

LaPrade, et al, "The Anatomy of the Medial Part of the Knee", J Bone Joint Surg Am, 89:2000-2010 (2007).

http://www.vjortho.com/2008/09/minimally-invasive-lateral-partial-knee-replacement. Webpage retrieved Sep. 15, 2015.

http://www.nuffieldhealth.com/treatments/unicompartmental-knee-replacement. Webpage retrieved Sep. 15, 2015.

* cited by examiner

TIBIAL COMPONENT

FIELD OF THE INVENTION

This invention relates to a tibial component, suitable for use in an orthopedic prosthesis, and more particularly in a prosthesis for resurfacing chondral surfaces of the knee joint.

BACKGROUND OF THE INVENTION

Various types of knee prostheses are known and used in the field of orthopedic surgery in treating a damaged or injured knee. Specifically, the present applicant is the inventor of ORTHOPEDIC PROSTHESIS described more fully in South African patent 2011/00697 filed 27 Jan. 2011, and claiming earliest priority 24 Jul. 2008, corresponding to PCT/IB2009/053224, as well as South African provisional patent application 2011/03673 dated 19 May 2011 entitled A SCORING SYSTEM AND METHOD FOR EVALUATING INJURY TO A JOINT which has matured into South African patent 2012/06206, each of which descriptions are incorporated herein in their entirety by reference.

Treatment options available in chondral resurfacing procedures of knee joints are unicompartmental knee arthroplasty (UKA) and total knee arthroplasty (TKA). In both UKA and TKA, a typical knee prosthesis comprises a metallic femoral component, a metallic tibial component and an ultra high molecular weight polyethylene (UHMWPE) spacer bearing (or bearing insert) disposed therebetween.

The femoral component, as the name suggests, is for fixation to the distal femur and the tibial component is for fixation to the proximal tibia.

Historically, the use of a fixed spacer bearing, wherein the spacer bearing is fixed to the tibial component, was the preferred combination. However, developments has seen a preference shift to a mobile spacer bearing, wherein the spacer bearing is allowed some degree of movement, in a slidable or partially rotatory fashion relative to the tibial component. It is now apparent that the selection of a mobile or fixed spacer bearing depends on the condition of the particular subject's knee and notably the degree of laxation of the knee ligamenture, which is adjudged intra-operatively. Ultimately, the final decision on whether to use a mobile bearing or fixed bearing, as well as which of UKA or TKA is appropriate, is made intra-operatively. For instance, a key indicator or contra-indicator as the case may be, would depend on a visual examination of the anterior cruciate ligament.

Further, UKA is the preferred form of treatment in diseased or injured knees having a chondral deficiency. In more severe presentations, a TKA is indicated. In either treatment option (viz. UKA or TKA), there is a preparatory step for prosthesis insertion that requires bone resection. Patient build and other anatomical considerations would indicate the selection of a particular size of femoral component and tibial component. The selection of a suitably sized spacer bearing is properly determined once the femoral and tibial components are inserted. This determination is finally done during the surgical procedure, and not before. Also, dependant on a visual inspection of the internal condition of the particular patient's knee, either a mobile or fixed spacer bearing is indicated. A distinct disadvantage may precipitate where a physician anticipates the use of a mobile spacer bearing, and an in-procedure inspection of the knee calls for the use of a fixed spacer bearing. In practice, both options are not readily available to the physician and a postponement of the operation is likely, as it is neither practical nor possible to include a full range of both mobile and fixed spacer bearings of different sizes in a single sterile pack. Such a pack would simply be too costly for most patients, and would represent wasteful expenditure. Also, fixed spacer bearings are manufactured at the factory and the bearings are usually not removable from the tibial component. The Applicant is aware of fixed bearing components that have clip-on spacer bearings. It use is still limited as explained above.

A further disadvantage with known prostheses may occur in instances where, due to rotation and flexion forces acting upon the spacer bearing between the femoral component and the tibial component, these spacer bearings are likely to wear out or dislocate with injury e.g. ligamentous rupture or in due course through normal use. Further, and dependant on other loading conditions acting on the spacer bearing, for instance where an inappropriately sized spacer bearing is utilized, the spacer bearing can prematurely wear out or succumb to abnormal damage. In such instance, revision surgery may be indicated, and removal of one or both of the femoral component and tibial component may be indicated. If the femoral component and/or tibial component are both in an acceptable condition, such removal would be disadvantageous in that the patient may be subject to yet further bone resection, is exposed to the future possibility of aseptic loosening of the prosthetic components where such components were successfully inserted, and may prematurely become a candidate for TKA where previously a UKA could have remained a viable option.

A need thus exists for a knee prosthesis that is capable of uniform application to any given patient, as well as a knee prosthesis that is minimally invasive, has a greater longevity, a reduced cost and shorter post-operative recovery time than known prostheses.

OBJECTS OF THE INVENTION

It is an object of the present invention to provide a tibial component suitable for universal application in an orthopedic prosthesis that at least partially overcomes the disadvantages associated with known prostheses.

It is a further object of the present invention to provide a tibial component that is both new and inventive relative to the prior art.

SUMMARY OF THE INVENTION

According to one aspect of the present invention, there is provided a tibial component, suitable for use in an orthopedic prosthesis, which prosthesis includes a femoral component and a spacer bearing, the tibial component comprising:
  a planar tibial plate having an upper bearing surface and a lower attachment surface; and
  the tibial plate further having at least one spacer bearing attachment means for removably securing the spacer bearing to the tibial plate.

The spacer bearing may be removably secured to the tibial component in order to prevent movement of the spacer bearing relative to the tibial component. The movement aforementioned may be rotational movement, translational movement, or both.

There is further provided, according to the invention, for the spacer bearing to include a concave surface for receiving the femoral component. The concavity on the spacer bearing may define a curvature of substantially 6°. The spacer bearing may alternatively include a planar surface for receiving the femoral component. Where the femoral component is brought to bear upon the spacer bearing having a concave surface, the intended use is for a prosthetic assembly having a mobile spacer bearing. Where the femoral component is brought to bear upon the spacer bearing having the planar surface, the intended use is for a prosthetic assembly having a fixed spacer bearing. It will thus be fully appreciated that the tibial component is adapted to interchangeably receive spacer bearings for either mobile- or fixed-bearing prosthetic assemblies.

The invention yet further provides for the orthopedic prosthesis to be particularly suitable for use in a human subject, and further particularly in a human knee.

The invention further provides for the tibial plate to include a flange located on the aspect of the tibial plate that is closest to the centerline of the knee. The flange may preferably be an orthogonal flange and may have an aperture located thereon. The aperture may be annular or oblique.

There may be further provided, according to the invention, for the attachment to be a primary attachment. The primary attachment may be in the nature of a screw and screw-threaded bore for locating and releasibly securing the spacer bearing onto the orthogonal flange and ultimately onto the tibial plate. Alternatively the primary attachment may be in the nature of a cantilevered pin having an elongate cylinder and an arcuate end thereon, defining a cantilevered snap-fit arrangement for releasibly securing the spacer bearing onto the orthogonal flange and ultimately onto the tibial plate.

The invention further provides for the primary attachment means to be complemented by a secondary attachment means. The secondary attachment means may be in the form of a locating member and a gripping member, each located on the spacer bearing. The locating member may be posteriorly disposed and snap-fits over a rim recess, also located on the tibial plate. The gripping member is located anteriorly and is for frictional engagement with a complementarily shaped holder, also located on the tibial plate. The locating member, rim access, gripping member and holder may collectively define the secondary attachment means.

The invention further extends to an orthopedic prosthesis assembly comprising a femoral component, a spacer bearing and a tibial component, wherein the tibial component comprises a planar tibial plate having an upper bearing surface and a lower attachment surface; and the tibial plate further having at least one spacer bearing attachment means for removably securing the spacer bearing to the tibial plate. The spacer bearing may include a concave surface thereon, or alternatively and a planar surface thereon.

The femoral component may include an elliptical body having an anterior member and a posterior member, and an internal femoral attachment surface; the femoral articular bearing surface and the internal femoral attachment surface having a substantially uniform cross-sectional curvature at any point along the length of the anterior member, thereby providing an increased radius of the internal femoral attachment surface and an increased cross sectional line of fixation to bony tissue; and the internal femoral attachment surface further defining a line of attachment extending across the substantially outer circumferential edge thereof.

The invention further extends to a revision method of re-surfacing chondral deficient surface areas in the knee joint, wherein the method is minimally invasive, including the step of utilizing and inserting an orthopedic prosthesis including a femoral component substantially as herein described, as well as a tibial component substantially as herein described, together with optional attachment means substantially as herein described.

BRIEF DESCRIPTION OF THE DRAWINGS

The invention will now be described in greater detail, by way of non-limiting example, with reference to the following drawings, in which.

DETAILED DESCRIPTION OF THE INVENTION

Figure 1:
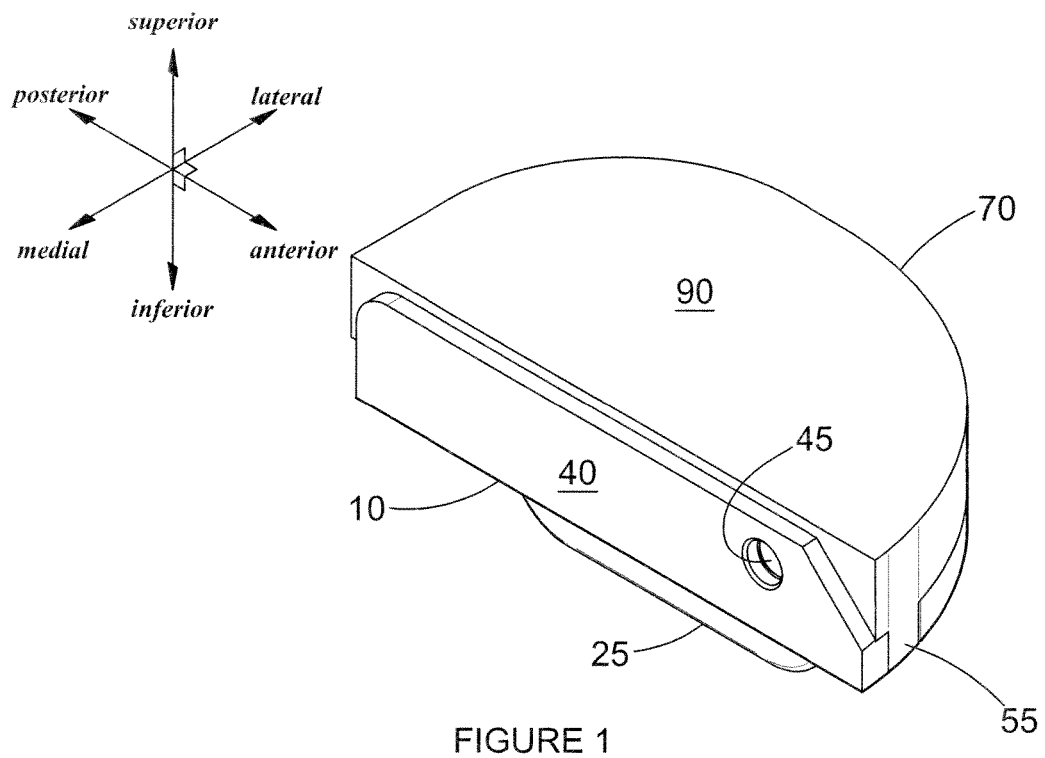
FIG. 1 shows a schematic perspective top view of a tibial component with engaged spacer bearing, according to one form of the invention.
Figure 2:
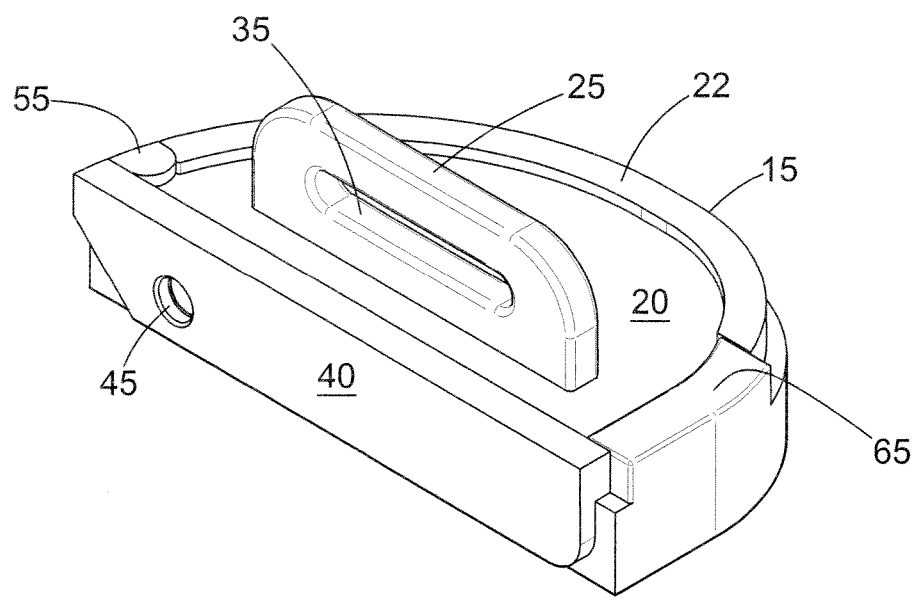
FIG. 2 shows a schematic perspective bottom view of the tibial component with engaged spacer bearing of the invention shown in FIG. 1.

In this specification, terms representative of anatomical references, such as medial, lateral, superior, inferior, and the like are to be construed as references to both the prosthesis, its respective parts, and to a patient's (not shown) natural anatomy. These terms are well-recognized and understood in the orthopedic and anatomical sciences and for purposes of this specification are to be given meanings consistent therewith.

In the drawings, like numerals refer to like parts, unless otherwise indicated.

Figure 3:
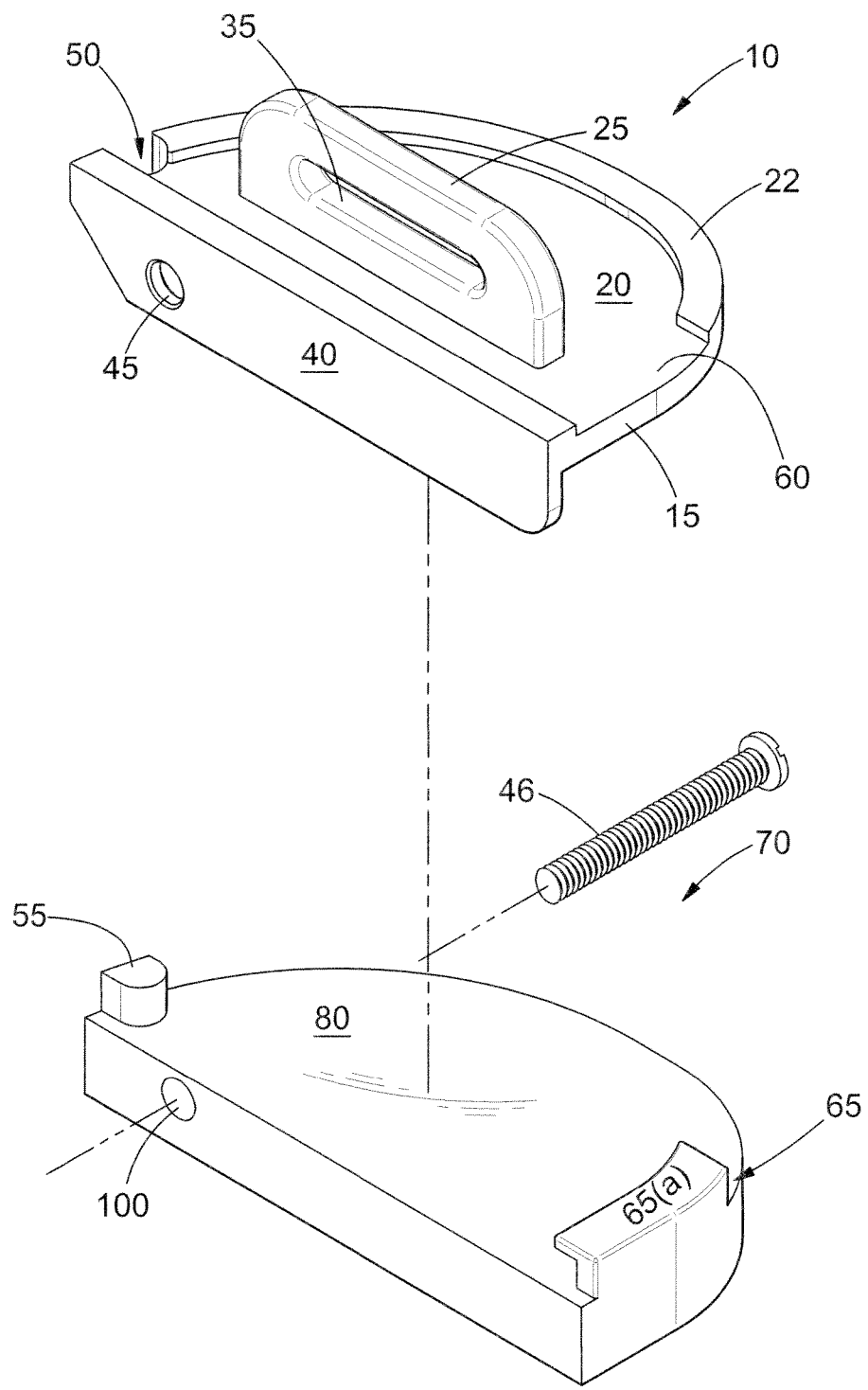
FIG. 3 shows an exploded schematic perspective bottom view of the tibial component with spacer bearing of the invention shown in FIG. 2.

Referring firstly to FIG. 3, and by way of a first non-limiting example of one form of the invention, reference numeral 10 generally refers to a tibial component 10 suitable for use in an orthopedic prosthesis (not shown), which prosthesis (not shown) includes a femoral component as described and exemplified in PCT/IB2009/053224 and a spacer bearing 90. The tibial component 10 comprises a planar tibial plate 15 having an upper bearing surface 30 and a lower attachment surface 20, and further has a spacer bearing attachment means for removably securing the spacer bearing to the tibial plate.

The planar tibial plate 15 is substantially D-shaped when viewed in plan view, the curved end thereof being disposed laterally (i.e. away from the centerline of the knee), while the opposite side (i.e. towards the midline) defines a straight edge. Tibial plate 15 has an upper bearing surface 30 (as can be seen more clearly in FIG. 4) for receiving and engaging the upper surface 90 of spacer bearing 70. Tibial plate 15 also defines a lower attachment surface 20 for attaching the tibial component 10 to a tibial plateau of a subject, generally shown in FIG. 8.

Tibial component 10 has an orthogonal flange 40 attached to and extending along the medial edge thereof antero-posteriorly, initially uniform in height posteriorly and thereafter tapering towards the tibial plate 15 anteriorly. Juxtaposed the taper apparent on orthogonal flange 40 is aperture 45 located anteriorly.

Lower attachment surface 20 has tibial anchor 25 extending inferiorly from, and centrally disposed on, lower attachment surface 20. A central, elongate aperture 35 is defined within tibial anchor 25.

Furthermore, lower attachment surface 20 has a raised surface in the form of a rim 22 that extends along the outer circumferential edge thereof. At the posterior end of tibial component 10, rim 22 terminates in a recessed portion of the raised surface to define a rim recess 60. Rim recess 60 is for receiving locating member 65 of spacer bearing 70, in a complementary engaging fashion relative to each other. This is intended for proper placement of spacer bearing 70 onto tibial component 10 in as quick and efficient a manner as possible during a resurfacing procedure.

Opposite rim recess 60, and at the anterior aspect of the tibial component 10, is holder 50 for receiving and removably securing gripping member 55 located on spacer bearing 70 in a mating engagement. Typically, the mating engagement is a first cantilevered snap-fit arrangement using a simple angled recess and hook (not shown). Preferably, the cantilevered snap-fit arrangement is of the permanent type.

On the anterior aspect of orthogonal flange 40 and juxtaposed the taper hereinbefore described is previously mentioned annular aperture 45, for receiving and anchoring fastening member 46 extending through bore 100 located on spacer bearing 70. In one embodiment of the present invention, securement of the fastening member 46 extending through bore 100 from a medially located entrance (not shown) on the spacer bearing 70, ultimately to partially anchor in annular aperture 45 is by way of a screw and complementary screw-threaded bore arrangement. The head of the screw seats in an angled rebate (not shown) extending about the periphery of the medially located entrance (not shown) on spacer bearing 70. It follows that annular aperture 45 and bore 100 are co-linearly disposed relative to each other, when spacer bearing 70 is engaged onto tibial component 10.

Figure 4:
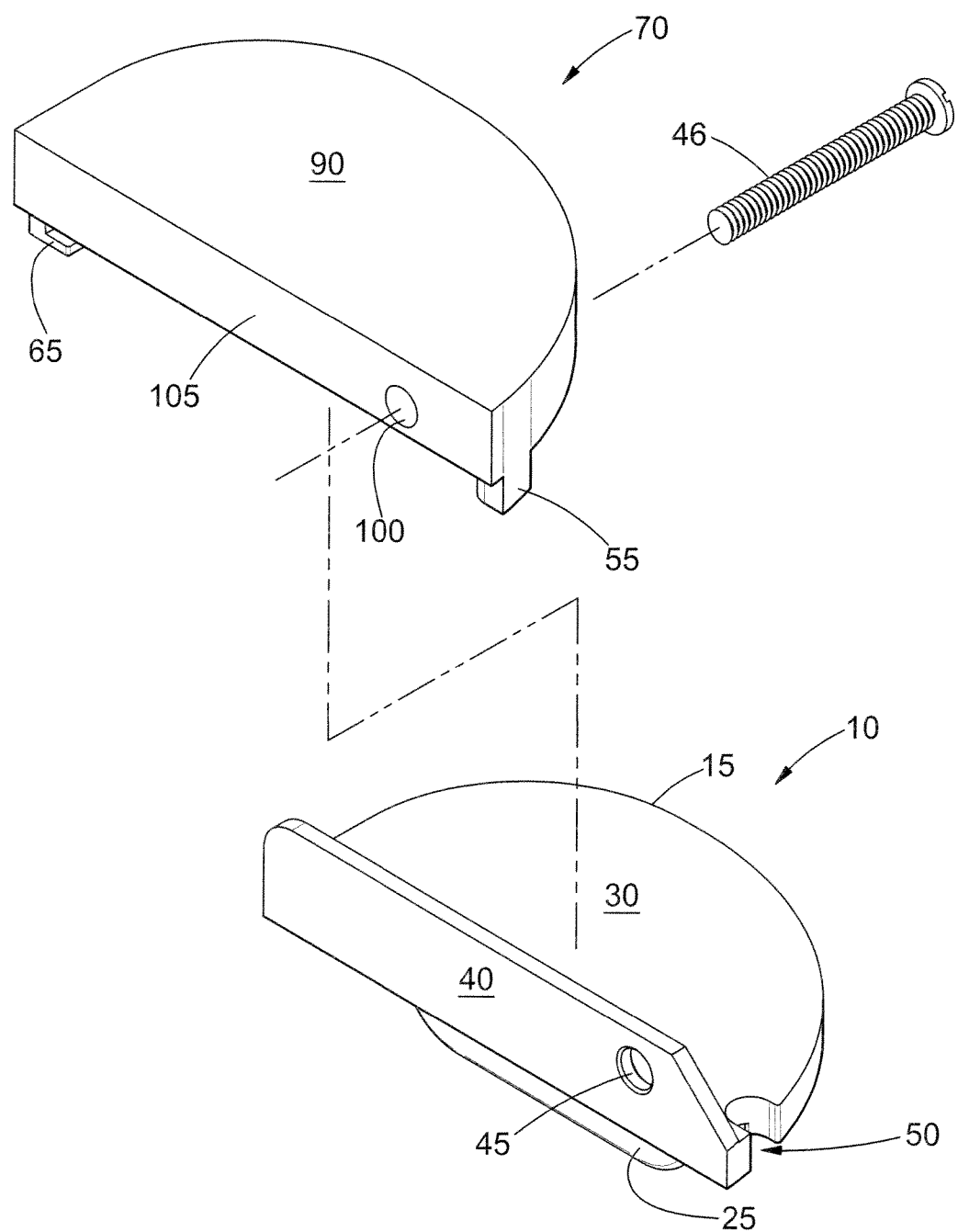
FIG. 4 shows a semi-exploded schematic perspective top view of the tibial component with spacer bearing of the invention shown in FIG. 1.

Referring next to FIGS. 3 and 4, spacer bearing 70 includes a body dimensioned to mirror the plan-view shape of tibial plate 15. The body aforementioned has an elongate sidewall 105 extending antero-posteriorly, and which terminates at an anterior end and a posterior end. Elongate sidewall 105 is for abutment with orthogonal flange 40, in use. The termination ends of sidewall 105 continue, initially perpendicular relative to the sidewall 105, and thereafter in a curved taper towards each other to ultimately meet, thereby defining a substantially D-shape in plan view.

In the described embodiment, upper surface 90 of spacer bearing 70 is typically planar on its surface and the femoral component (not shown) is brought to bear thereon. The lower surface 80 of spacer bearing 70 is brought to bear on the upper bearing surface 30 of tibial plate 15. From the anterior end of lower surface 80, grip formation 50 extends inferiorly. Opposite to the anterior end, and at the posterior end of lower surface 80, is locating member 65, also extending downwardly and terminating in an inwardly extending flange 65(a) that seats in rim recess 60.

Figure 5:
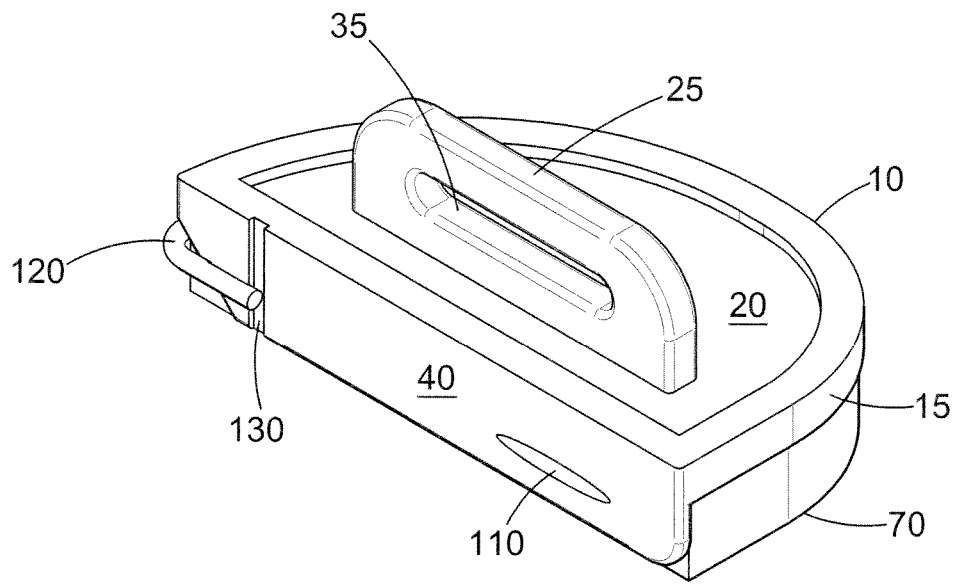
FIG. 5 shows a schematic posterior perspective bottom view of a tibial component with engaged spacer bearing, according to an alternate form of the invention.
Figure 6:
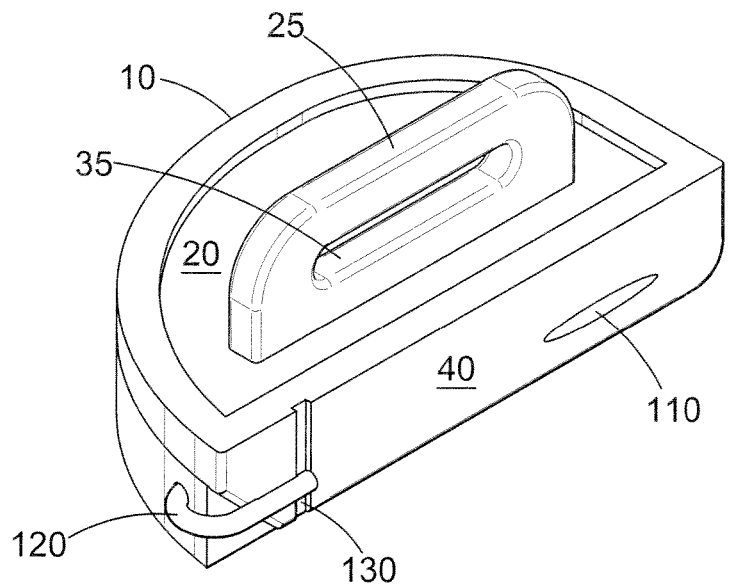
FIG. 6 shows a schematic anterior perspective bottom view of a tibial component with engaged spacer bearing, according to an alternate form of the invention.
Figure 7:
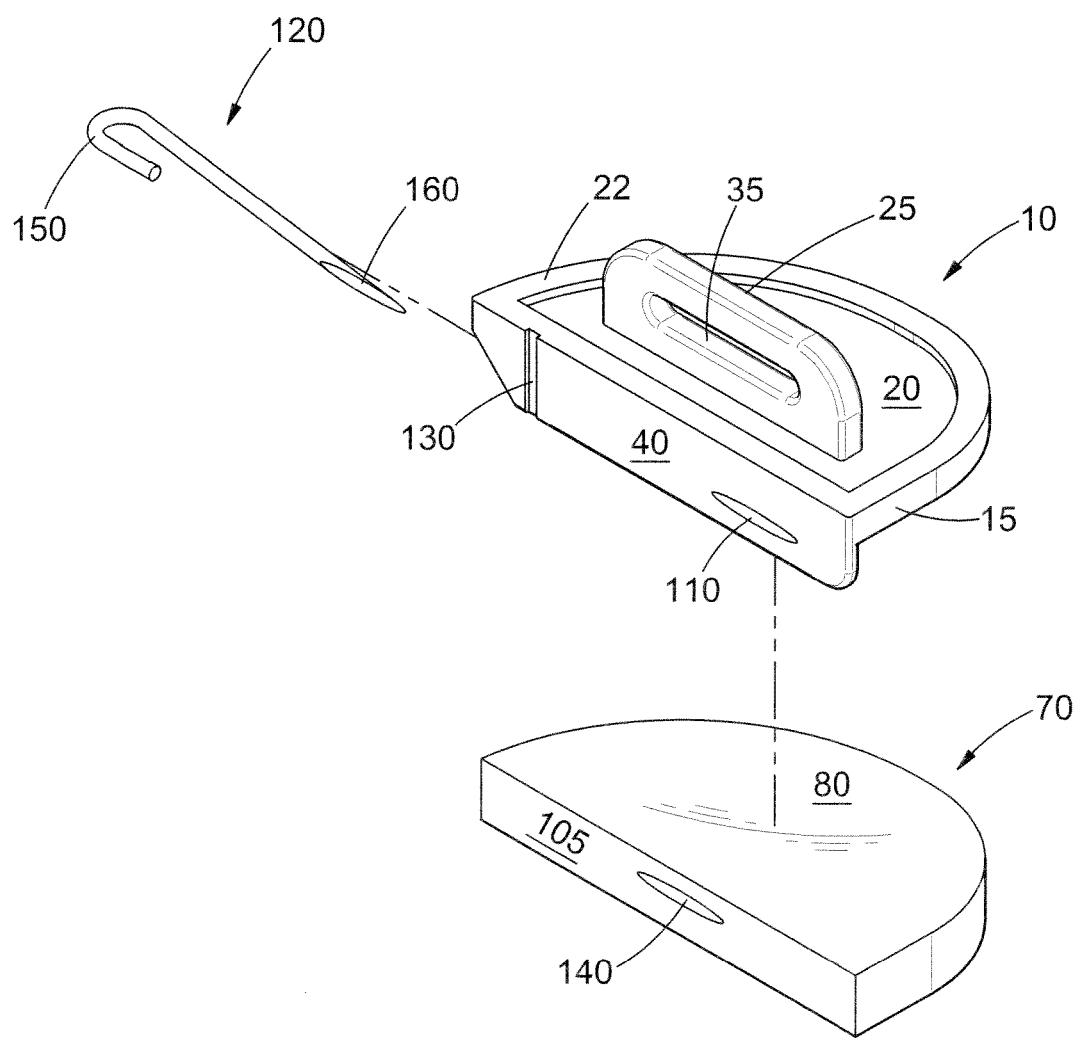
FIG. 7 shows an exploded schematic perspective bottom view of a tibial component with spacer bearing, according to the invention shown in FIG. 5.

By way of second, non-limiting example of an alternative form of the present invention, FIGS. 5, 6 and 7 show alternative forms of a spacer bearing and fastening means to the embodiment described above, but which alternative falls wholly within the scope of the present disclosure. In this example, annular aperture 45 is substituted by oblique aperture 110, which extends obliquely through orthogonal flange 40 towards the posterior end thereof. Oblique aperture is in co-linear relation with oblique bore 140 located on spacer bearing 70 and which extends obliquely from a position located on the anterior aspect of spacer bearing 70, and terminates on sidewall 105.

Further, according to this alternative example, at the anterior end of orthogonal flange 40 is linear recess 130 which extends perpendicularly to orthogonal flange 40. A further substitution in this example relates to securing member 120 as alternative to fastening member 46. The securing member 120 is an elongate cylinder having an arcuate end 150 and a pointed locating end 160. The arcuate end 150 terminates in a second cantilevered snap-fit arrangement using a hook for locating in linear recess 130.

It is thus readily understood that the combination of fastening member 46/bore 100/annular aperture 45, and (in the alternative) securing member 120/oblique aperture 110/oblique bore 140, are all in the collective representative of the aforementioned spacer bearing attachment means (unreferenced).

It will be appreciated that the immobility or mobility of spacer bearing 70 in the alternate example will depend wholly on the use, or non-use, respectively of alternate fastening member 120. Where a mobile bearing is intended, spacer bearing 70 has a concave upper bearing surface (having a 6° curvature) for receiving the femoral component. The spacer bearing attachment means is not utilized and the spacer bearing 70 is allowed freedom of movement relative to the tibial plate as is known in the art. Central to both described examples is the immediate interchangability of a mobile spacer bearing prosthetic assembly to that of a fixed spacer bearing prosthetic assembly. In the case of the former, this is though the omission of fastening member 46 or securing member 120, as well as the placement of spacer bearing 70 onto the tibial component 10 having a concave upper bearing surface to face and receive a load from the femoral component (not shown). In the case of the latter, spacer bearing 70 having a planar upper bearing surface is engaged onto tibial component 10 while, inter alia, fastening means 46 or securing member 120 is used to secure the spacer bearing 70 onto tibial component 10.

Figure 8:
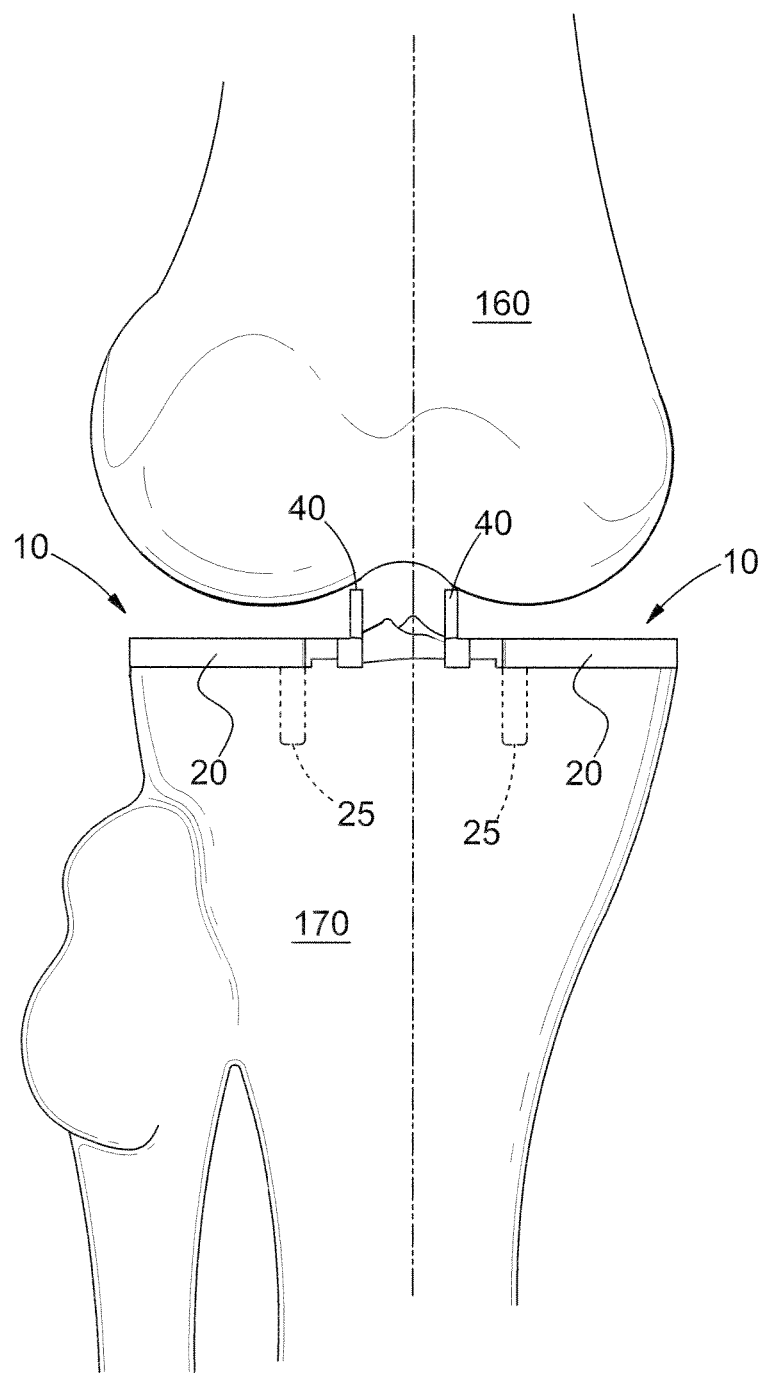
FIG. 8 shows a side-by-side frontal schematic view of the invention in situ in a human knee.

It will also be readily appreciated that the tibial component 10 is particularly suited for use in a human knee (not shown), the articulation of which is shown generally in FIG. 8. Femur 160 is articulated with tibia 170, and it is envisioned by the applicant that the tibial component 10 can be used for either the medial knee compartment or the lateral knee compartment, as depicted more clearly in FIG. 8.

In use, a physician will make a small (approximately) 10 centimeter incision at the appropriate spot on a subject's knee in order to expose the inner knee articulation. Once the femoral condyle and tibial plateau (both not shown) have been suitably prepared by placement of the femoral component (not shown) and tibial component 10, respectively on these locations, a suitably sized spacer bearing is selected for insertion. According to the initial example described hereinabove, the posterior end of the spacer bearing 70 is advanced onto tibial plate 15 until locating member 65 locates onto rim recess 60. Once located thereon, gripping member 55 is physically depressed into grip formation 50 and the spacer bearing is thus properly located onto tibial plate 15, with sidewall 105 in abutment with orthogonal flange 40. A suitably sized fastening member 46 such as a screw is introduced into complementary threaded bore 100 from the medially located bore entrance (not shown) on spacer bearing 70 (having a planar bearing surface) and advanced through bore 100 to locate and anchor in annular aperture 45. The spacer bearing 70 is now affixed to the tibial component 10 and represents a fixed prosthetic assembly. The procedure is completed after suturing of the subject's knee.

Similarly, where a physician opts to use the fastening means represented by the combination of securing member 120/oblique aperture 110/oblique bore 140, in such instance, the physician advances alternate fastening member 120 through anteriorly located oblique bore 140 located on spacer bearing 70 (having a planar upper bearing surface), until the pointed locating end appears visible through oblique aperture 110. At this point, arcuate end 150 will be flush against the corner defined by the anterior aspect and sidewall 105, the second cantilevered snap-fit arrangement having been engaged, thereby securing the spacer bearing 70 onto tibial component 10. This also represents a fixed bearing arrangement or fixed prosthetic assembly.

If it is apparent intra-operatively that a mobile spacer bearing arrangement would be more suitable to the subject's needs, the spacer bearing 70 having a concave upper bearing surface is selected is merely placed onto tibial plate 15 in mating engagement with tibial plate 15. The use of spacer bearing attachment means is avoided and no limitation in the movement of the spacer bearing 70 relative to the tibial plate 15 will result. This arrangement thus represents a mobile bearing prosthetic assembly.

It will yet further be appreciated that the invention extends to the use of a tibial component 10 as herein described, together with a femoral component defining a femoral articular bearing surface and a spacer bearing as herein described disposed therebetween, the femoral component further including an elliptical body having an anterior member and a posterior member, and an internal femoral attachment surface, the femoral articular bearing surface and the internal femoral attachment surface having a substantially uniform cross-sectional curvature at any point along the length of the anterior member, thereby providing an increased radius of the internal femoral attachment surface and an increased cross sectional line of fixation to bony tissue, the resurfacing of chondral deficient surface areas in knee joints.

A person skilled in the art will readily appreciate that a physician would be able to replace spacer bearing 70 as and when the occasion calls for same, such as when the spacer bearing is worn or damaged, without disturbing the tibial component or the femoral component. Also, given the relative ease of insertion of the spacer bearing into the existing prosthesis, patient exposure is minimized. Furthermore, the spacer bearing will assume the identity of a readily replaceable part of the prosthesis, thereby prolonging the life of existing prosthetic devices, and in particular those prosthetic assemblies associated with UKA procedures.

Although certain forms of the invention only have been described herein, it will be understood by any person skilled in the art that other modifications or variations of the invention are possible. For instance, the spacer bearing attachment means need not be limited to the two examples described herein, and can embody any alternative and suitable spacer bearing attachment means that achieves the purpose of fixing the spacer bearing 70 to the tibial component 10. Additionally, preference is given to the use of the tibial component 10, together with a femoral component that defines a uniradial curvature. A femoral component having a poly-radial curvature may be substituted for use, where suitable. Such modifications and/or variations are therefore to be considered as falling within the spirit and scope of the present invention as herein described.

The invention claimed is:

1. A tibial component, suitable for use in an orthopedic prosthesis, which prosthesis includes a femoral component and a spacer bearing, wherein the tibial component is shaped to be used in at least one of the medial and lateral compartments of a knee, the tibial component comprising:
a planar tibial plate having an upper bearing surface and a lower bone connecting surface, the tibial plate being adapted to interchangeably in situ receive anteriorly-loaded spacer bearings for either mobile- or fixed-bearing prosthetic assemblies;
the tibial plate further having at least one anteriorly located spacer bearing attachment means for removably securing the spacer bearing to the tibial plate; and
wherein the interchangeability of the spacer bearing between mobile and fixed assemblies is immediate or subsequent to a revision procedure, without disturbing bone connecting surfaces of the tibial component.

2. The tibial component as claimed in claim 1, wherein the spacer bearing is removably secured to the tibial component thereby preventing movement of the spacer bearing relative to the tibial component.

3. The tibial component as claimed in claim 2, wherein the movement of the spacer bearing is rotational movement, translational movement, or a combination of both rotational and translational movement.

4. The tibial component as claimed in claim 1, wherein the spacer bearing includes a concave surface for receiving the femoral component.

5. The tibial component as claimed in claim 4, wherein the femoral component is brought to bear upon the concave surface of the spacer bearing, for use in a mobile spacer bearing prosthetic assembly.

6. The tibial component as claimed in claim 1, wherein the spacer bearing includes a planar surface for receiving the femoral component.

7. The tibial component as claimed in claim 6, wherein the femoral component is brought to bear upon the planar surface of the spacer bearing, for use in a fixed spacer bearing prosthetic assembly.

8. The tibial component as claimed in claim 1, wherein the tibial plate includes an orthogonal flange located on an aspect of the tibial plate that is closest to the centerline of the knee, the orthogonal flange having an annular or obliquely disposed aperture located thereon.

9. The tibial component as claimed in claim 8, wherein the attachment means is a primary attachment in the form of a screw and screw-threaded bore for locating and releasibly securing the spacer bearing onto the orthogonal flange and ultimately onto the tibial plate.

10. The tibial component as claimed in claim 9, wherein the primary attachment is in the form of a cantilevered pin having an elongate cylinder and an arcuate end thereon, defining a cantilevered snap-fit arrangement for releasibly securing the spacer bearing onto the orthogonal flange and ultimately onto the tibial plate.

11. The tibial component as claimed in claim 9, wherein the primary attachment is complemented by a secondary attachment means, which secondary attachment means is collectively defined by a locating member, a rim recess, a gripping member and a holder.

12. The tibial component as claimed in claim 11, wherein the locating member and a gripping member are each located on the spacer bearing.

13. The tibial component as claimed in claim 12, wherein the gripping member is located anteriorly on the spacer bearing and is for frictional engagement with a complementarily shaped holder located on the tibial plate.

14. The tibial component as claimed in claim 13, wherein the spacer bearing may include a concave surface thereon, or alternatively and a planar surface thereon, further alternatively a combination of planar and concave surfaces located thereon on opposite sides of the spacer bearing.

15. The tibial component as claimed in claim 13, wherein the femoral component includes an elliptical body having an anterior member and a posterior member, and an internal femoral attachment surface; the femoral articular bearing surface and the internal femoral attachment surface having a substantially uniform cross-sectional curvature at any point along the length of the anterior member, thereby providing an increased radius of the internal femoral attachment surface and an increased cross sectional line of fixation to bony tissue; and the internal femoral attachment surface further defining a line of attachment extending across the substantially outer circumferential edge thereof.

16. The tibial component as claimed in claim 11, wherein the locating member is posteriorly disposed on the spacer bearing and is for snap-fitting over a rim recess located on the tibial plate.

17. The tibial component as claimed in claim 1, comprising a femoral component, a spacer bearing and the tibial component, wherein the tibial component comprises a planar tibial plate having an upper bearing surface and a lower attachment surface, the tibial plate being adapted to interchangeably in situ receive spacer bearings for either mobile- or fixed-bearing prosthetic assemblies; and the tibial plate further having at least one anteriorly located spacer bearing attachment means for removably securing the spacer bearing to the tibial plate.

18. The tibial component as claimed in claim 1, for use in a human subject, and in particular in a human knee.

19. A revision method of re-surfacing chondral deficient surface areas in the knee joint, wherein the method is minimally invasive, including the step of utilizing and inserting an orthopedic prosthesis including a femoral component substantially as claimed in claim 1, as well as a tibial component substantially as herein described.

* * * * *